(12) United States Patent
Globerman

(10) Patent No.: US 6,641,609 B2
(45) Date of Patent: Nov. 4, 2003

(54) MEDICAL STENTS, APPARATUS AND METHOD FOR MAKING SAME

(75) Inventor: Oren Globerman, Holon (IL)

(73) Assignee: Medtronic AVE, Inc., Santa Rosa, CA (US)

(*) Notice: Subject to any disclaimer, the term of this patent is extended or adjusted under 35 U.S.C. 154(b) by 0 days.

(21) Appl. No.: 10/192,072

(22) Filed: Jul. 9, 2002

(65) Prior Publication Data

US 2002/0177892 A1 Nov. 28, 2002

Related U.S. Application Data

(63) Continuation of application No. 09/533,879, filed on Mar. 22, 2000, now Pat. No. 6,428,570.

(51) Int. Cl.⁷ .................................................. A61F 2/06
(52) U.S. Cl. ........................................................ 623/1.15
(58) Field of Search ............................. 623/1.15–1.18, 623/1.1, 1.2, 1.21, 1.5, 1.51–1.54; 606/194, 195, 200

(56) References Cited

U.S. PATENT DOCUMENTS

| | | |
|---|---|---|
| 4,776,337 A | 10/1988 | Palmaz |
| 4,816,028 A | 3/1989 | Kapadia et al. |
| 4,856,516 A | 8/1989 | Hillstead |
| 4,893,623 A | 1/1990 | Rosenbluth |
| 4,969,458 A | 11/1990 | Wiktor |
| 4,994,071 A | 2/1991 | MacGregor |
| 5,019,085 A | 5/1991 | Hillstead |
| 5,104,404 A | 4/1992 | Wolff |
| 5,116,365 A | 5/1992 | Hillstead |
| 5,135,536 A | 8/1992 | Hillstead |
| 5,178,618 A | 1/1993 | Kandarpa |
| 5,234,457 A | 8/1993 | Anderson |
| 5,282,824 A | 2/1994 | Gianturco |
| 5,293,879 A | 3/1994 | Vonk et al. |
| 5,314,472 A | 5/1994 | Fontaine |
| 5,354,309 A | 10/1994 | Schnepp-Pesch et al. |
| 5,356,423 A | 10/1994 | Tihon et al. |
| 5,366,473 A | 11/1994 | Winston et al. |
| 5,383,892 A | 1/1995 | Cardon et al. |

(List continued on next page.)

FOREIGN PATENT DOCUMENTS

| | | |
|---|---|---|
| EP | 0 540 290 | 5/1993 |
| WO | WO96/14808 | 5/1996 |
| WO | WO96/26689 | 9/1996 |

OTHER PUBLICATIONS

Fischman et al. A Randomized Comparison of Coronary–Stent Placement and Balloon Angioplasty in the Treatment of Coronary Artery Disease, The New England Journal of Medicine, 331:496–501 (1994).

Serruys et al., A Comparison of Balloon–Expandable–Stent Implantation with Balloon Angioplasty in Patients with Coronary Artery Disease, The New England Journal of Medicine, 331:489–495 (1994).

*Primary Examiner*—Michael J. Milano
*Assistant Examiner*—Tan-Uyen T. Ho

(57) ABSTRACT

An expandable stent and stent graft having a small initial diameter, flexibility along its longitudinal axis prior to expansion and a large expanded and rigid Local stain on the stent material is minimized, as and after the balloon is expanded. More particularly, the stent has rotation joints having minimal strain during stent expansion. The stent is substantially the same length before and after expansion and being flexible longitudinally when constrained, it is easy to locate. A method of manufacturing stents is described comprising rotation of a tube beneath a moving film, with light passing through the film onto the tube, at selected locations. A laser scanning system for stent manufacture is also disclosed.

23 Claims, 12 Drawing Sheets

U.S. PATENT DOCUMENTS

| | | |
|---|---|---|
| 5,389,106 A | 2/1995 | Tower |
| 5,421,955 A | 6/1995 | Lau et al. |
| 5,443,496 A | 8/1995 | Schwartz et al. |
| 5,449,373 A | 9/1995 | Pinchasik et al. |
| 5,507,767 A | 4/1996 | Maeda et al. |
| 5,514,154 A | 5/1996 | Lau et al. |
| 5,527,354 A | 6/1996 | Fontaine et al. |
| 5,540,712 A | 7/1996 | Kleshinski et al. |
| 5,540,713 A | 7/1996 | Schnepp-Pesch et al. |
| 5,549,662 A | 8/1996 | Fordenbacher |
| 5,549,663 A | 8/1996 | Cottone, Jr. |
| 5,554,181 A | 9/1996 | Das |
| 5,591,197 A | 1/1997 | Orth et al. |
| 5,591,198 A | 1/1997 | Boyle et al. |
| 5,607,442 A | 3/1997 | Fischell et al. |
| 5,607,445 A | 3/1997 | Summers |
| 5,613,981 A | 3/1997 | Boyle et al. |
| 5,630,829 A | 5/1997 | Lauterjung |
| 5,636,641 A | 6/1997 | Fariabi |
| 5,643,312 A | 7/1997 | Fishcell et al. |
| 5,653,727 A | 8/1997 | Wiktor |
| 5,674,276 A | 10/1997 | Anderson et al. |
| 5,681,346 A | 10/1997 | Orth et al. |
| 5,697,971 A | 12/1997 | Fischell et al. |
| 5,725,572 A | 3/1998 | Lam et al. |
| 5,728,158 A | 3/1998 | Lau et al. |
| 5,733,303 A | 3/1998 | Israel et al. |
| 5,735,893 A | 4/1998 | Lau et al. |
| 5,741,327 A | 4/1998 | Frantzen |
| 5,755,776 A | 5/1998 | Al-Saadon |
| 5,759,192 A | 6/1998 | Saunders |
| 5,766,238 A | 6/1998 | Lau et al. |
| 5,776,161 A | 7/1998 | Globerman |
| 5,911,754 A | 6/1999 | Kanesaka et al. |
| 6,033,433 A | 3/2000 | Her et al. |
| 6,053,940 A | 4/2000 | Wijay |
| 6,063,113 A | 5/2000 | Kavteladze et al. |
| 6,106,548 A | 8/2000 | Roubin et al. |
| 6,221,100 B1 * | 4/2001 | Strecker .................... 623/1.22 |
| 6,547,819 B2 * | 4/2003 | Strecker .................... 623/1.22 |

\* cited by examiner

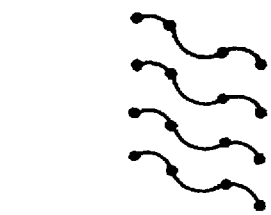
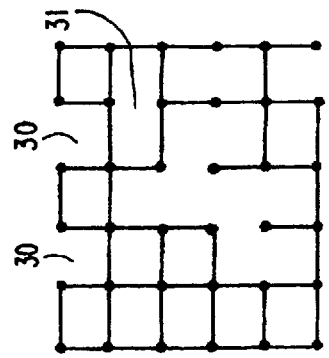
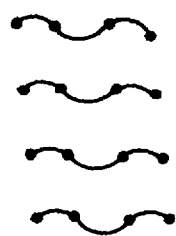
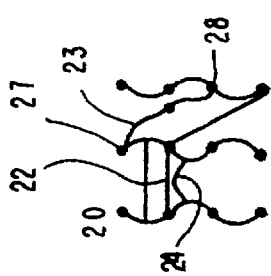
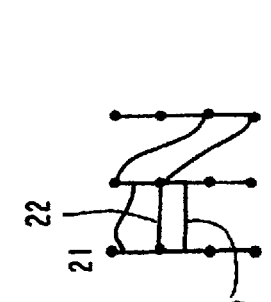
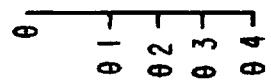

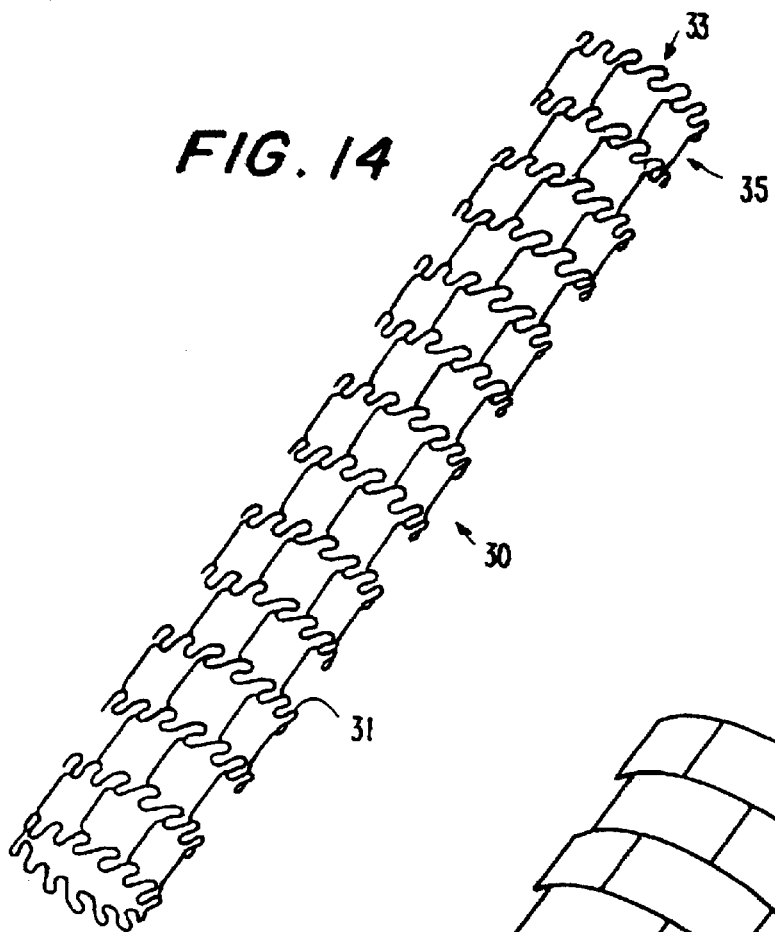
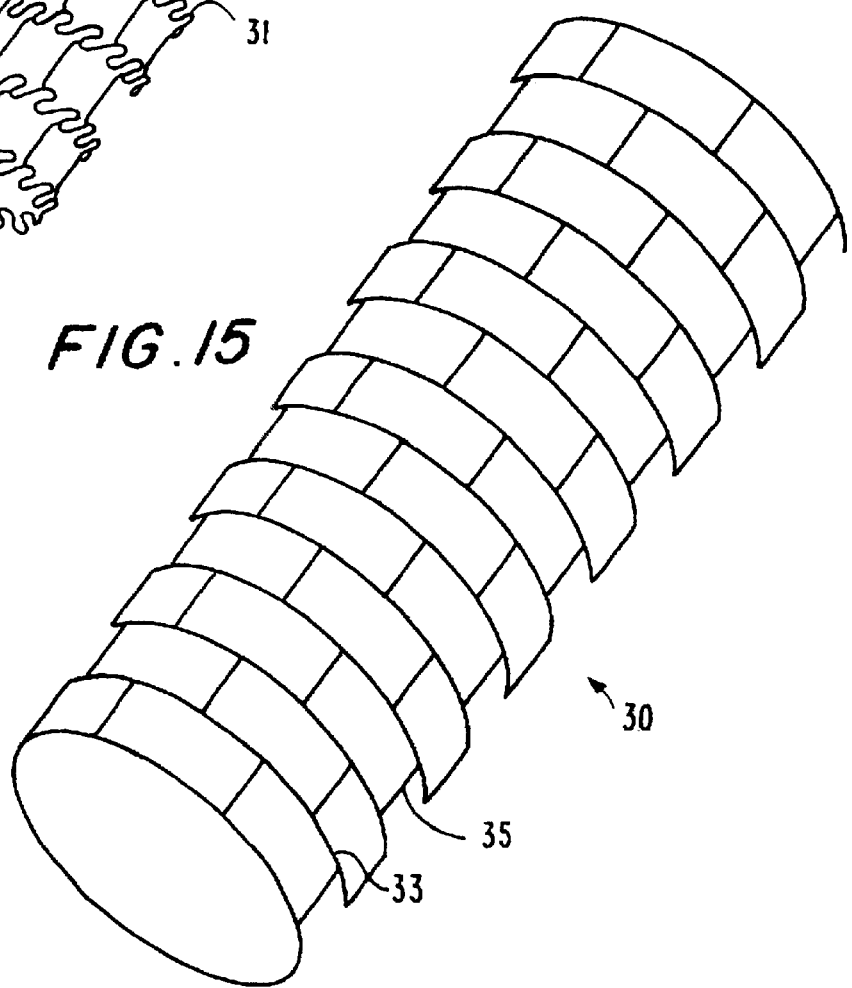

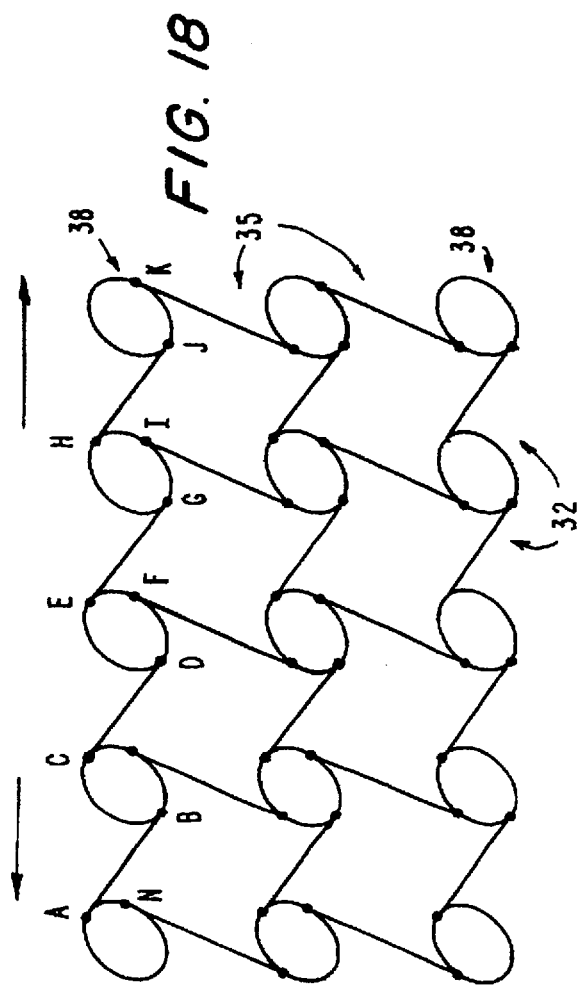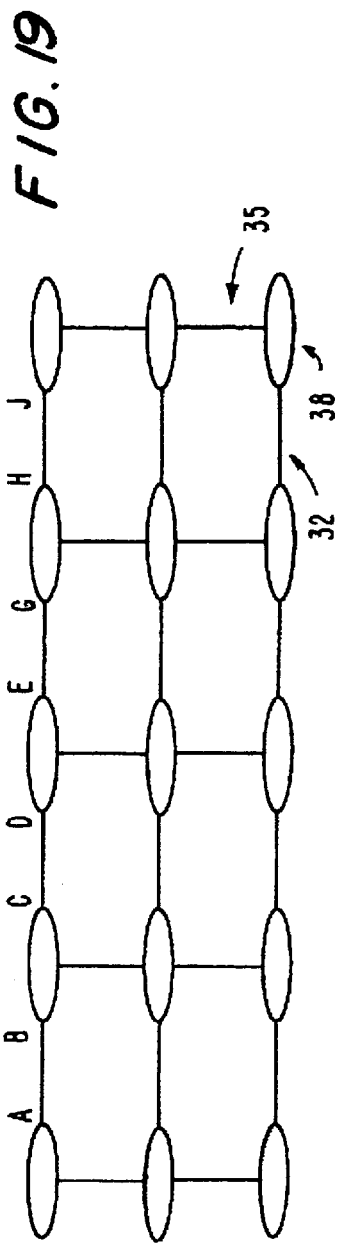

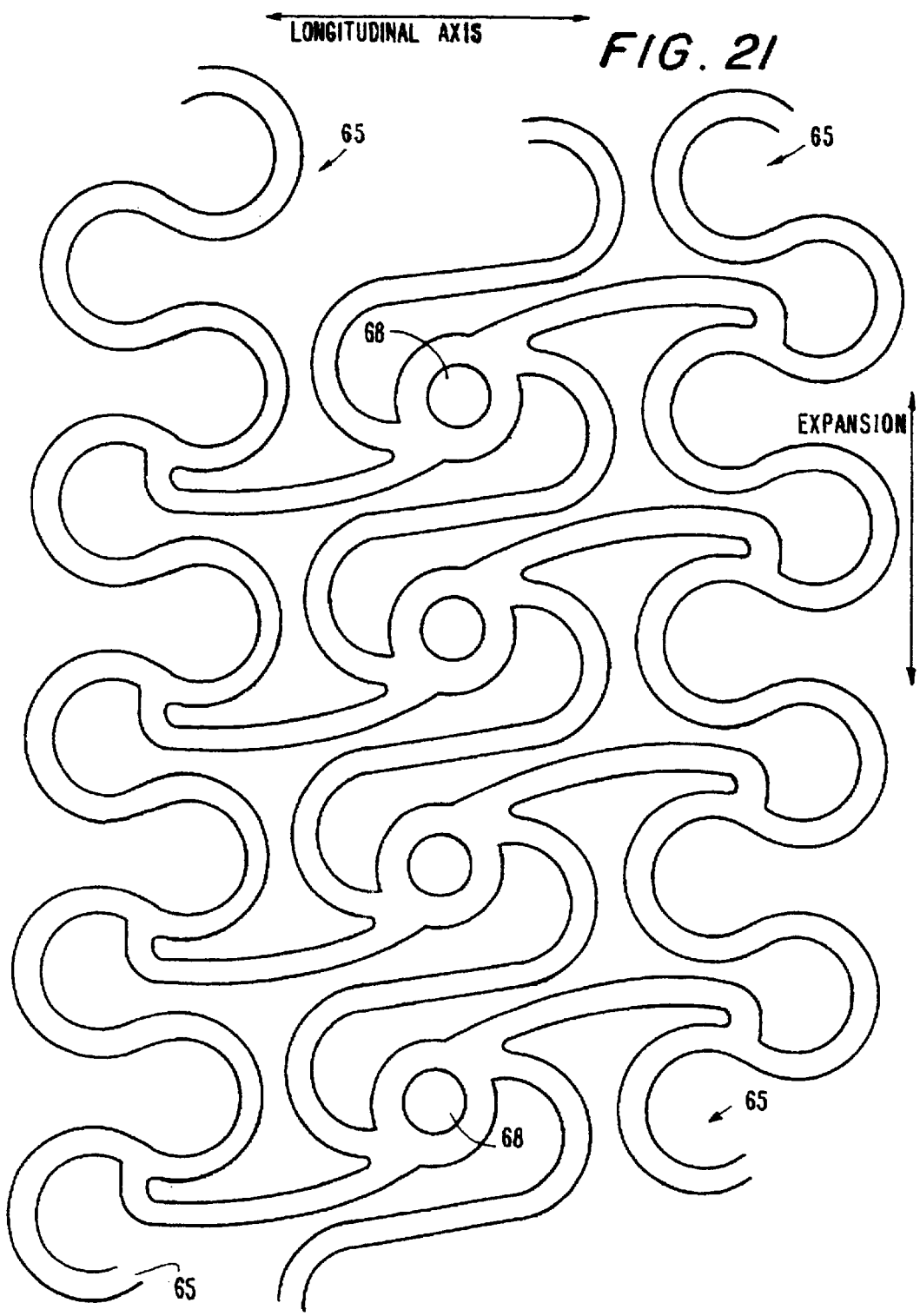

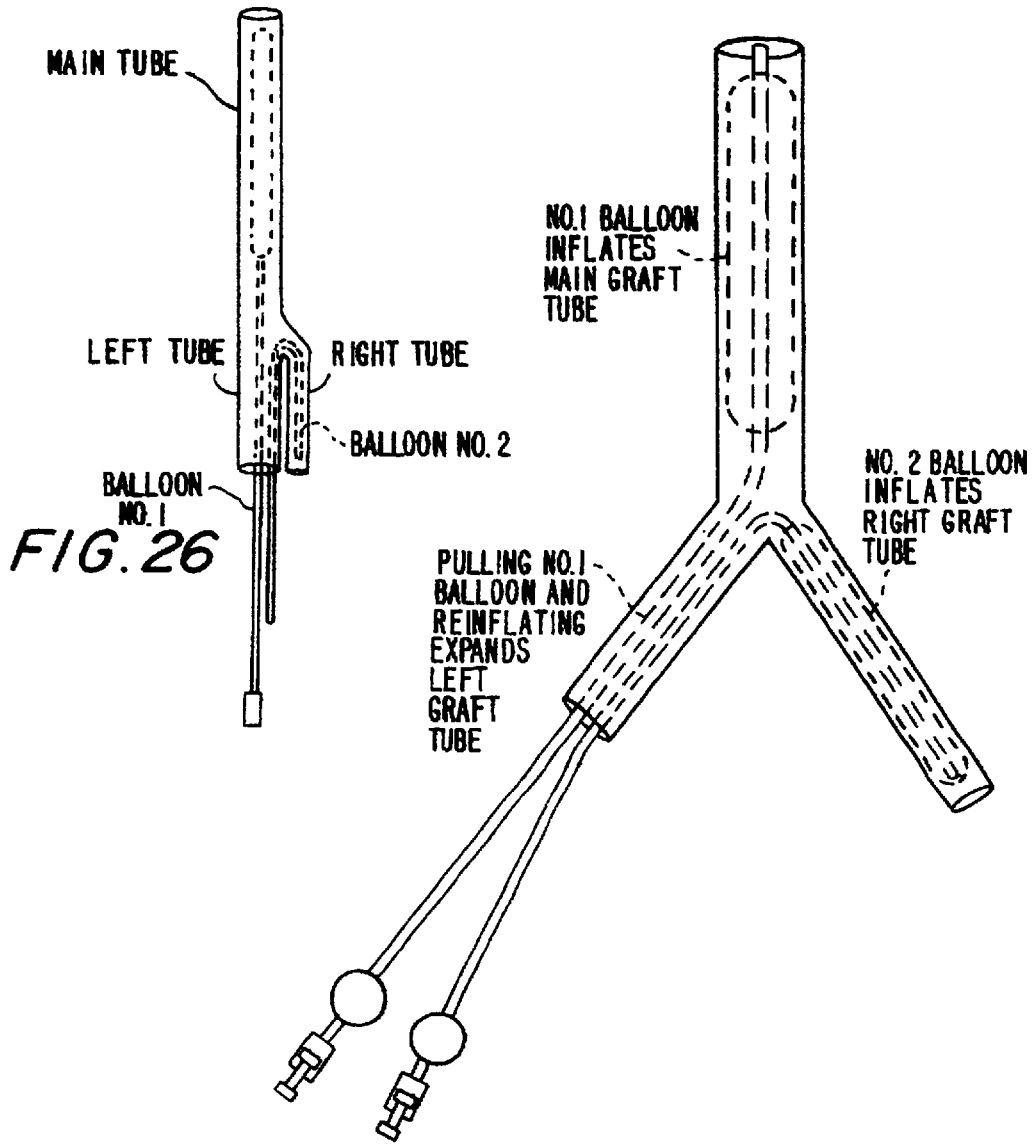

MEDICAL STENTS, APPARATUS AND METHOD FOR MAKING SAME

This is a continuation application Ser. No. 09/533,879, filed on Mar. 22, 2000, now U.S. Pat. No. 6,428,570.

FIELD OF THE INVENTION

The present invention relates to an improved stent and stent graft for use in constricted body tubes, and for widening a stenosis in a body cavity such as in an artery, in the bile duct, esophagus, and so forth. The present invention also relates to stent production technology, and a method for manufacture of the improved stent device.

BACKGROUND OF THE INVENTION AND DESCRIPTION OF THE PRIOR ART

Intraluminal endovascular stenting is a method by which a prosthesis is inserted into a body tube and expanded so as to reopen a collapsed vessel wall and prevent the wall from recollapsing into the lumen. Endovascular stenting is particularly useful for arteries which are blocked or narrowed and is an alternative to surgical procedures that intend to bypass the occlusion.

Previous structures used as stents or intralumninal vascular grafts have included coiled stainless steel springs; helical wound spring coil made from shape memory alloy; expanding metal stents formed in a zig-zag pattern; diamond shaped, rectangular shaped, and other mesh and non-mesh designs. Some of the stents currently available employ a self expanding concept, whereby stent expansion is primarily achieved by removing a restraint mechanism holding the stent in a constricted configuration. Other stents in the prior art are delivered to the site by a balloon catheter system, and primarily employ balloon dilation to achieve proper stent expansion.

Problems with this variety of stents is inadequate radial force to maintain expansion; inappropriate scaffolding of tissue to the wall; pre-dilated longitudinal rigidity which negatively impacts on stent delivery; and shortening of the stent as a consequence of radial expansion. Pre-dilation stent longitudinal rigidity is a significant shortcoming, and prevents the threading of the stent through long tortuous vessels and lesions. Shortening of the stent is also a problem, as it is important that the stent cover the entire lesion to minimize the risk of post-operative complications. Obviously, therefore, there is a need for a long yet flexible stent that will provide the appropriate scaffolding effect, will be able to track well in-curved vessels, will not shorten during radial expansion, and yet will have sufficient outward radial force to hold the artery open, even in the presence of hard calcified lesions. The stent disclosed herein overcomes these disadvantages. No stent having all of the desired features appears to exist, prior to this invention which achieves most of these properties.

As is well known, a traditional alternative to conventional vascular surgery has been percutaneous transluminal balloon angioplasty (PCTA). In this procedure, the angioplasty balloon is inflated within the stenosed artery to create, through shearing and mechanical trauma, a larger inner lumen. This process, while successful in achieving a larger lumen in most cases, can sometimes cause local tears, dissections and protrusion of plate into the lumen so that vessel blockage is caused rather than the desired vessel opening. In addition, the phenomenon of elastic recoil and intimal growth following arterial dilation often causes late restenosis (within six months) in more than about 30% of the patients undergoing the angioplasty balloon procedure. Because of the fear of the acute complication of sudden occlusion (abrupt closure), a surgical backup is needed in most places where PTCA is performed, This is yet another limitation of the mechanical balloon dilatation procedure.

It has been shown that stenting results in excellent acute results with adequate scaffolding of tears to the wall of the artery and with generation of a large inner lumen. This large inner lumen, initially present after stenting, has a lower restenosis rate after the procedure, as shown in the STRESS (N. Engl. J. Med. 1994; 331:L 496–501) and BENESTENT (N. Engl. J. Med. 1994; 331: 489–95) studies. While the inner lumen achieved using the self-expanding stents depends on the sizing of the stents relative to the vessel, the inner lumens that can be achieved with balloon expandable stents depend both on the size and radially expanding pressure of the balloon. The inner lumens achievable with balloon expandable stents can be further increased with further inflation of the balloon.

One of the major complications associated with stent use has been thrombosis. The problem occurs most commonly between day 2 and 6 of the implantation, but may also occur as late as 3 weeks after stenting. This complication is caused by clotting of the stent and is associated with high morbidity and mortality. It has been recently shown that the better the stent apposition against the wall and the larger the lumen is, the less likely that this complication will occur. In addition, it is very important that the stent cover the entire lesion since the existence of obstructions before or after the stent may also cause a complication.

The current balloon expandable stents have the significant limitation of relative, longitudinal rigidity during delivery, and so do not allow for a very long stent to traverse the usual curves in the artery. This longitudinal rigidity during delivery is sought to be avoided by devices taught in the patents to Wolff (U.S. Pat. No. 5,104,404) and to Pinchasik (U.S. Pat. No. 5,449,373) in which the rigid Palmaz stent sections are connected together with flexible connections. For this reason, it is required that the stent be long (to allow treatment of long and flexible upon insertion to site (to allow passage to and through tortuous locations) but yet have large radial force to unblock the vessel and excellent scaffolding so as to be able to hold the atherosclerotic material against the wall, even in bends and in hard calcified lesions. The stent should also allow for further balloon expansion if further lumen enlargement is required at particular locations.

In U.S. Pat. No. 5,104,404, Pinchasik attempts to address some of the shortcomings of the prior art by teaching the use of different connectors (articulation) between the rigid Palmaz stent segments, enabling more flexibility between the rigid parts.

It would be highly desirable, however, to have a stent having few or no longitudinally rigid parts so that it will be homogeneously flexible along its entire longitudinal axis when delivered on the catheter. Furthermore it would be extremely desirable to eliminate the longitudinal shortening of the stent during radial expansion to minimize stent misplacement.

Furthermore, in Palmas' stents marketed by Johnson & Johnson, as well as in others, during plastic deformation of the stent (i.e. balloon expansion) the strain is concentrated at small zones. This limits the properties of the material that can be used as well as the radial force and the expansion rate. By distributing the strain over large zones, a less thick annealed material can be used to both avoid deterioration of the radial force of the stent when expanded, and to reduce the stent's constricted profile. There are obvious advantages to reduced stent thickness.

According to the prior art method of manufacturing stents, the material is originally flat. The screen-like material is then rolled into a cylinder shape and laser welded or otherwise connected to form a tube—the weld running the length of the longitudinal axis. This is a difficult and expensive manufacturing procedure. It also leads to a potential lack of uniformity. The present invention, a new method of stent manufacture, as will be explained, results in a more uniformly expandable stent, one not having a weld line formed after mesh formation.

Patents which relate to the field of stent geometry are as follows: U.S. Pat. Nos. 5,354,309; 4,776,337; 5,356,423; 5,383,892; 5,178,618; 5,449,373; and 5,104,404.

SUMMARY OF THE INVENTION

The object of the present invention is to provide a stent which has flexibility substantially along its longitudinal axis when constrained on a catheter to allow it to easily pass through and along highly curved body vessels and fluid-carrying tubes.

It is further an object of the invention to supply the constricted stent (i.e., before balloon expansion) with a minimum diameter to ease its passage for placement through a minimal diameter vascular port as well as to enable it to enter through narrow lumens of constricted body tubes.

It is further an object of the invention to provide a stent geometry which results in a more homogenous distribution of the strain on the stent material, reducing the maximum strain on the stent when expanded so that less material can be used. Subjecting less material to the same balloon-expanding force can result in greater radial expansion. This allows both a greater expansion ratio for the stent and smaller stent wall thickness.

It is further an object of this invention to allow a stent geometry and proper material to provide additional stent diameter expansion by elongation of the stent material (such as tantalum) and not by changing the shape of the stent.

It is further an object of the invention to provide a stent which does not substantially change in length as the stent diameter is expanded during balloon inflation.

A further object of the present invention is to provide a method for fabricating stents and, in particular, the stents disclosed herein.

It is a further object of the invention to supply the stent with a graft material to be a stent graph as well as a stent graft of Y-shape for aortic aneurism.

BRIEF DESCRIPTION OF THE DRAWINGS

(In FIGS. 2–11, the interconnections between the adjacent radial rings of the stent are not shown.). A ring of the stent resembles a lock washer, an undulating ring shape;

FIG. 3 is a partial section of a stent showing the pair of adjacent radial rings of FIG. 2, after expansion of the stent;

FIG. 4 is a partial section of a pair of radial rings of a second embodiment of a stent, without longitudinal connection (for ease of illustration) before expansion, having points or dots on the rings which will rotate 90° upon stent expansion;

FIG. 5 is a partial section of another embodiment of a stent showing a pair of radial rings, before expansion, having points or dots on the rings which will rotate 180° upon expansion;

FIG. 6 is a partial section of a pair of radial rings of another embodiment of the stent, again, before expansion, having points, or dots on the rings which will rotate 360° upon expansion;

FIG. 7 is a partial section of a pair of radial rings of another embodiment of the stent, both before (on the right side) and after (on the left side) expansion, having two types of dots or points on the rings which will rotate through angles of 45° and 90° respectively, upon expansion;

FIG. 8 shows a partial section of a pair of radial rings of another embodiment of the stent, before expansion, in which the radial rings have two types of dots or points on the rings which will rotate through angles of 45° and 180°, respectively, upon expansion;

FIG. 9 shows two pairs of radial rings of yet another embodiment of the stent, before expansion, in which adjacent rings are constructed with mirror images of each other;

FIG. 10 shows four radial rings in which neighboring rings are offset, i.e., have constructions which differ by an angle of rotation from each other. The "z" and "θ" angles are shown on the axis; the "θ" axis, corresponds to the angle "θ" illustrated in FIG. 1;

FIG. 11 shows a partial section of four rings of yet another embodiment of a stent, before expansion;

FIG. 12 shows a graphical depiction of two types of longitudinal connections between neighboring radial rings of a stent, the right side of the Figure being before stent expansion;.

FIG. 13 shows a graphical representation of a section of an expanded stent which has been constructed such that some of the radial segments and some of the longitudinal connections are deliberately omitted during manufacture;

FIG. 14 is a perspective view of a stent according to the present invention with the stent in its constricted form, prior to expansion and wherein the connections between adjacent rings of the stent are straight;

FIG. 15 is a perspective view of the stent of FIG. 14 with the stent in its expanded form;

FIG. 18 shows an enlarged partial section of another embodiment of a stent in which the stent joints (between the adjacent rings) are circular, and the stent is in its constricted form, prior to the expansion. Individual rings are formed with the circular joints, as well;

FIG. 19 shows the portions of the stent of FIG. 18 in its expanded form. Points A, B, C, D, E, F, G, H, I, J and K have been shown on both FIGS. 18 and 19 (opposed, offset U-shapes) to illustrate relative movement and location, a consequence of stent expansion;

FIG. 20A shows the stent in a constricted form;

FIGS. 21 and 22 show partial sections of a stent with undulated (opposed, offset U-shapes) radial strips or segments as in FIG. 20A, forming the rings, yet with the circular connectors being hollow. The rings are connected by longitudinal segments;

FIG. 22 shows another embodiment with undulating rings, longitudinal connectors and simple intersections;

FIG. 25 is a schematic representation of a Y-tube stent graft in the open position, according to the present invention;

FIG. 26 is a schematic representation of a Y-tube stent graft in the closed configuration.

FIG. 28 shows that the repetitive "peaks" and "valleys" of adjacent rings are offset by about 150 to 160 degrees.

DETAILED DESCRIPTION OF THE INVENTION

The present invention relates to a novel stent construction. The stent geometry allows both longitudinal flexibility of the stent when the stent is constricted to its initial narrow diameter for threading through the body vessel, and maximum rigidity, after the stent is expanded to its final large diameter, for supporting the body vessel wall. The geometry of the stent is further designed to allow the stent to remain substantially the same length before and after expansion and even zero strain on the connection points.

Moreover, as will be described below, the stent geometry allows a substantially homogeneous distribution of strain on the stent material. This allows for less local strain (e.g. on the connection points securing neighboring radial rings of the stent to longitudinal segments and forming the rings themselves), and thus a smaller stent profile is achieved. It aids stent delivery, inside body tubes. Also, the less material used for the stent, the less rejection of the body to the foreign material. This geometry of the stent also allows a further diameter expansion by material stretching such as tantalum which allows up to about 40% elongation. The stent's further expansion is better achieved by the homogeneous distribution of stress, a result of the new geometry.

Figure 1:
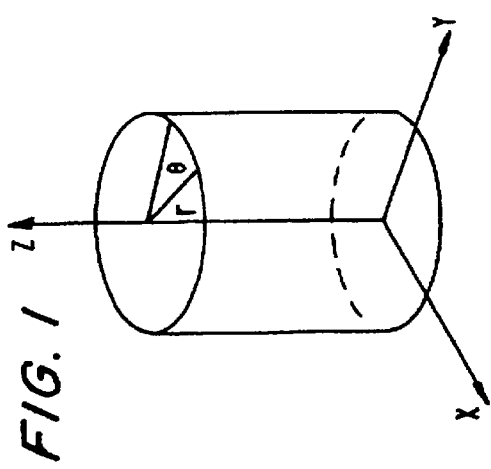
FIG. 1 is an elevational view of a stent (shown as a cylinder for illustrative purposes) in cylindrical coordinates.

FIG. 1 shows a cylindrical stent with orthogonal cylindrical coordinates (R, θ, Z). Coordinate Z corresponds to the longitudinal central axis of the stent. When Z=O, the stent's longitudinal end is described. The stent length, its longitudinal axis, is Z. Radius r refers to the radius of the stent from the longitudinal axis of the stent to the outer circumference of the stent. Radius r, of course, changes with stent dilation during deployment of the balloon or other expansion of the stent radius by another mechanism (e.g., memory metal). As shown in FIG. 14, the stent 30, in its constricted state (i.e. before expansion), is a hollow cylinder, or is tube-like. The hollow cylinder has windings 31 on its surface joined together at points to form the radial rings. The stent has longitudinal flexibility, when in its constrained diameter, and allows for radial expansion. As shown in FIG. 15, the stent 30, in its expanded state, has the radial rings opened, the windings uncurl from their constricted to their expanded state, providing a larger radius r for the hollow cylinder of the stent construction.

Figure 2:
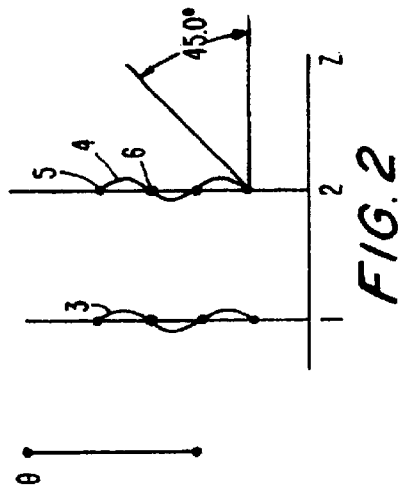
FIG. 2 is a partial section of a stent, showing a pair of radial rings, unconnected in the longitudinal direction (for illustration) and showing a stent before expansion, having points or dots on the rings which will rotate 45° upon expansion due to balloon inflation.

FIG. 2 shows adjacent radial rings (1) and (2) of a stent. In the Figure (and in all of FIGS. 2–11) each ring is shown without the longitudinal connections which are provided between adjacent rings. The longitudinal connections are shown, for example, in FIGS. 14–16. Radial rings (1) and (2) are each originally, i.e., before expansion, curved, with the curves of the rings crossing the Z=constant axis of the ring. Each curved ring has dots or points (e.g. dot or point (3) on ring 1, and dots or points (4), (5) and (6) on ring 2, on its curves During outward expansion of the stent, dots (5) and (6) rotate. During the rotation of the dots, no deformation occurs in the dots. During expansion, dot (5) rotates in a 45° angle clockwise manner and dot (6) rotates in a 45° angle counterclockwise manner, thereby resulting in stent geometry shown in FIG. 3.

Figure 3:
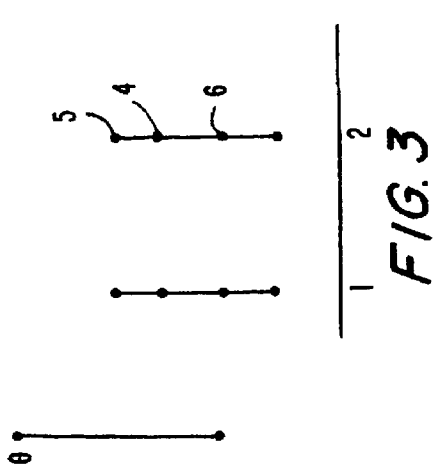

FIG. 3 shows two radial rings 1 and 2 of FIG. 2 after maximal stent diameter expansion. Although the connections on the longitudinal axis are not shown in the Figure, the resulting shape of the connected radial rings, after maximal expansion, is a cylindrical mesh of rectangular boxes (similar to screening material). A hollow cylinder of rectangular boxes is formed. The rectangular mesh can be seen by reference to FIG. 15.

Figure 5:
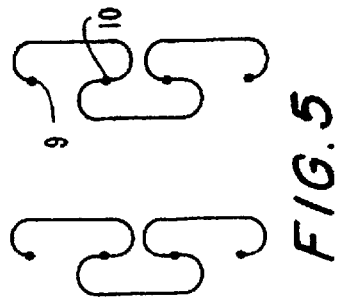
Figure 4:
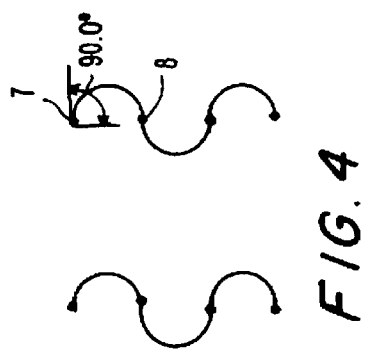
Figure 6:
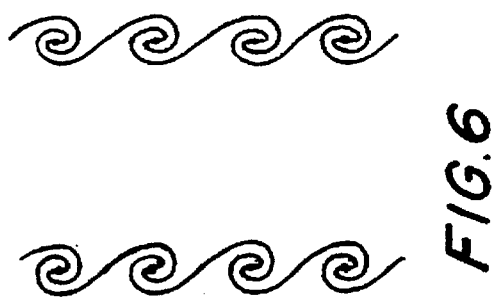
Figure 8:
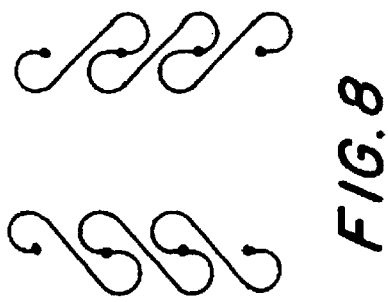

As shown in FIGS. 4, 5 and 6, stents are depicted formed of rings 1 and 2 with dot rotation angles of 90°, 180°, and 360°, respectively, (and by the same principle, any intermediate angle) thereby achieving different levels of radial expansion.

Figure 7:
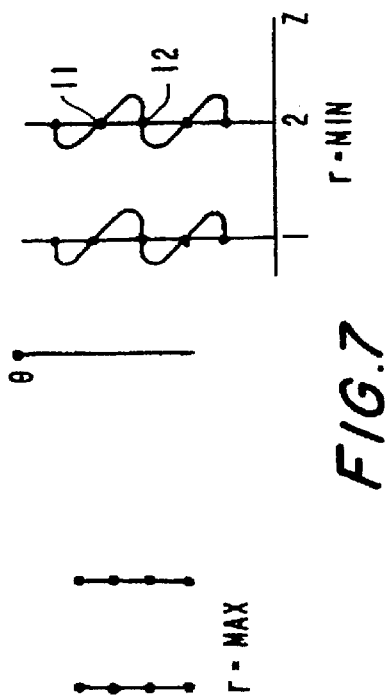

In FIG. 7, the angle of rotation of the rotating dots is 45° clockwise (11) and 90° counterclockwise (for connecting dot 12).

Figure 9:
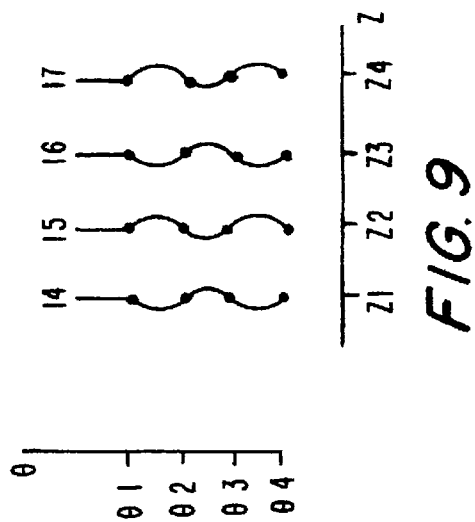

In FIG. 9, it is shown that, in addition to achieving rotation around rotation dots or points at any radial line (Z1, Z2, . . . ), it is also possible to rotate each ring in the opposite direction of rotation of its neighbor ring, i.e. like mirror images. Dots (14) and (16) will rotate counterclockwise while dots (15) and (17) will rotate clockwise. Again, flexibility of stent design is achieved.

Figure 27:
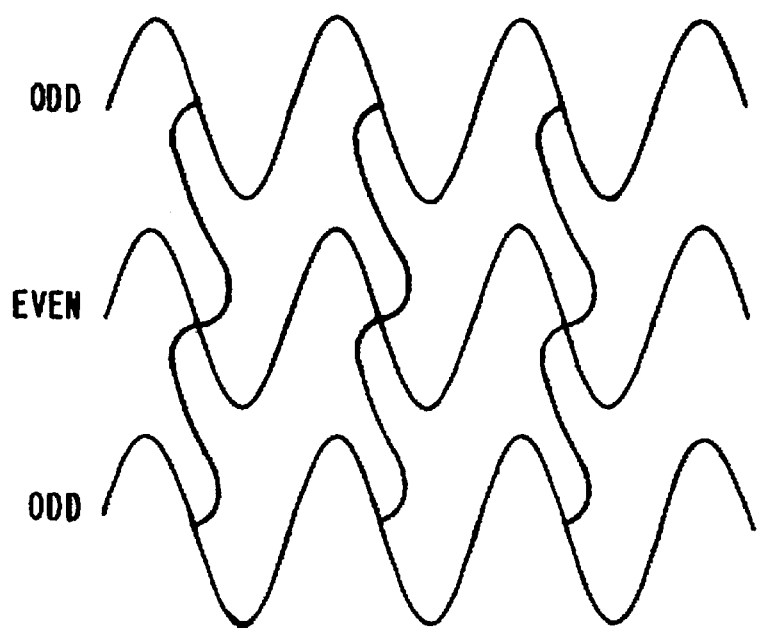
FIG. 27 is an enlarged partial view of the stent of the present invention, in an embodiment where all the rings are in phase.
Figure 28:
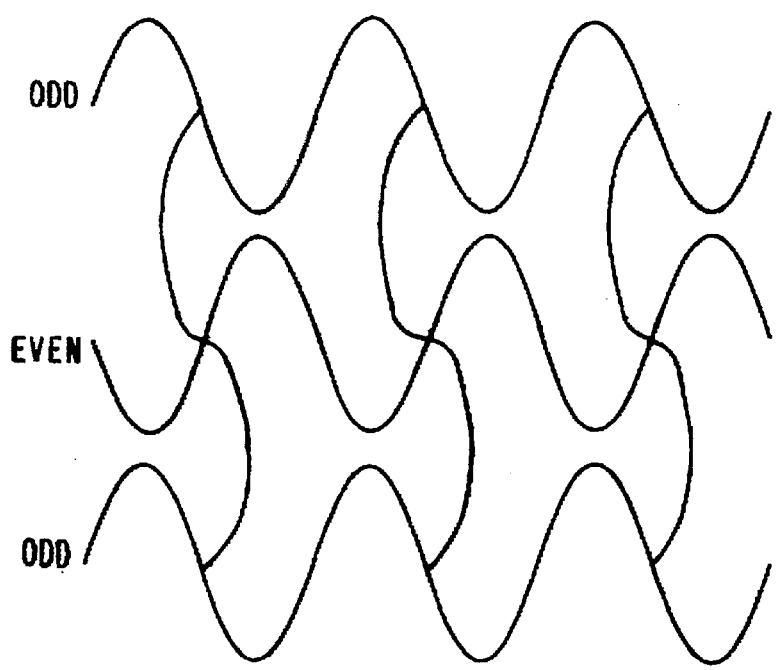
FIG. 28 is an enlarged partial view of the stent of the present invention, in an embodiment where adjacent or paired rings are 180 degrees out of phase with one another. Of course, as will be appreciated from the description of the drawings and of the invention, all angles between 0 degrees and 180 degrees can be used for the lateral offset of the "peaks" and "valleys" of the adjacent rows.

In FIG. 10, a stent design is shown (four rings without ring interconnects for ease of illustration), as in FIG. 2, but having an angle of rotation or offset between the radial rings along the stent's longitudinal axis Z. FIG. 27 shows an embodiment of the invention where adjacent rings have their "peaks" and "valleys" in phase with one another while FIG. 28 shows an alternate embodiment of the invention where the rings are arranged in pairs with each ring of the pair is the mirror image of the other ring of the pair, i.e., the "peaks" and "valleys" of the rings are 180 degrees out of phase. Of course, according to the present invention, the offset between adjacent of pairs of rings can incrementally vary from a low of 0 degrees, as shown in FIG. 27 to a high of 180 degrees, as shown in FIG. 28.

FIG. 11 shows, instead of having close radial loops as in FIG. 2–10, the present invention can also be practiced with a coil shape on which all rotation dots will be on the line that $Z=K \times \theta$.

In FIG. 12, ring 20 is circumferentially longer than the distance between two rings Z1 and Z2 (distance between adjacent rings), and has shape 21 (left side of FIG. 12) after stent expansion, leaving the stent length substantially unchanged. Longitudinal connector 22, whose length is equal to the distance between the two rings, does not deform during stent expansion. Connection 24 is a curved shape before stent expansion, and changes to a straight line 25 after stent expansion. The longitudinal connections can be between two dots (27 and 28) that are not necessarily placed along a line that is parallel to the Z axis.

FIG. 13 shows that for longitudinal flexibility (important for stent deployment to the site) segments of longitudinal connectors 30 and/or sections of the rings 31, can be selectively omitted for some parts of the stent.

Figure 16:
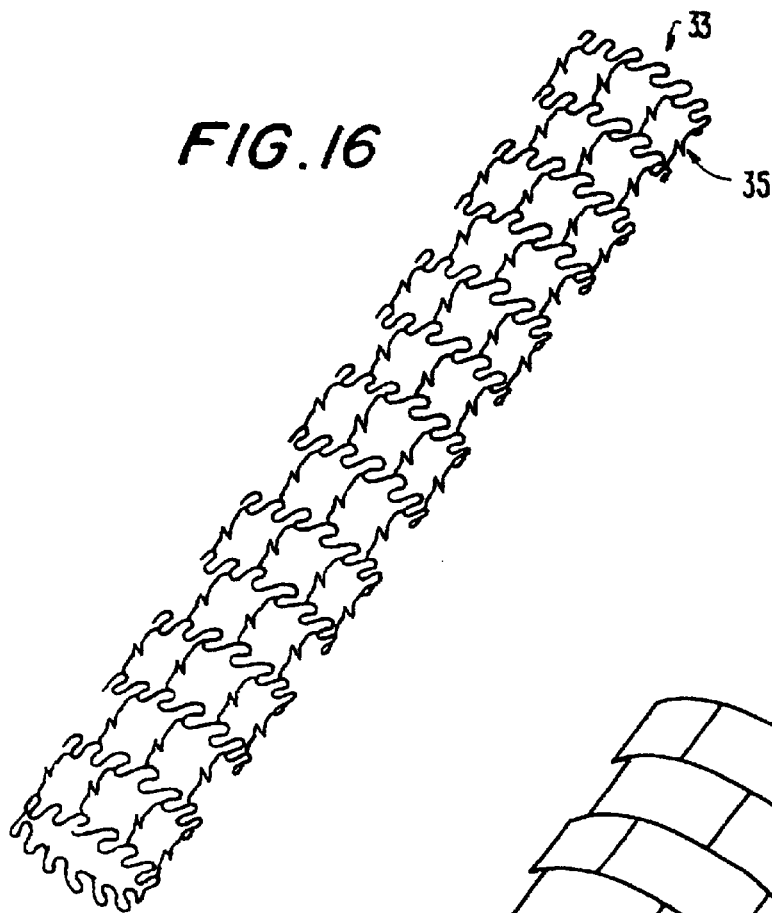
FIG. 16 is a perspective view of another embodiment of a stent in which the connections between the adjacent rings of the stent are also curved. The stent is shown in the constricted form prior to expansion.
Figure 17:
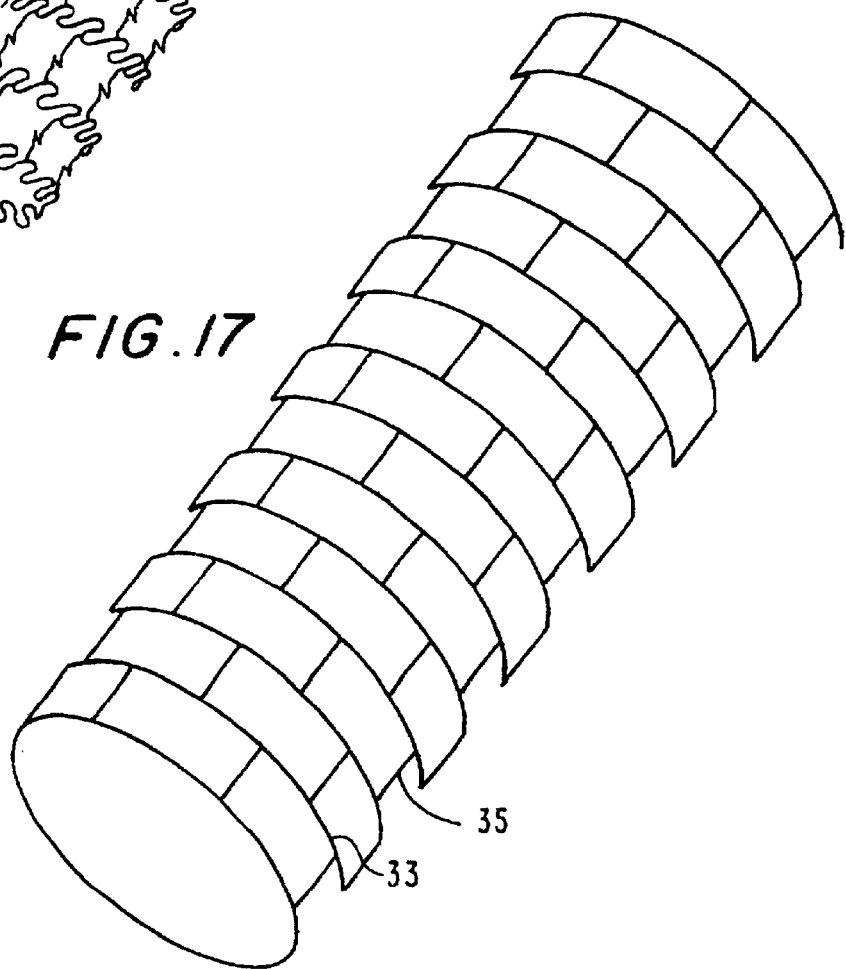
FIG. 17 is a perspective view of the stent of FIG. 16 in its expanded form.

FIGS. 14 and 16 show two embodiments of the stents, in accordance with the present invention, each in a constricted configuration. As shown, the radial rings 33 are connected with longitudinal connectors 35. In FIG. 14, the longitudinal connectors are straight (both before and after expansion), while in FIG. 16, the longitudinal connectors are curved (before expansion). FIG. 15 shows the stent 30 of FIG. 14 in an expanded configuration, after inflation by a balloon. FIG. 17 (not to scale) similarly depicts the expanded configuration of the stent of FIG. 16. As can be seen from the Figures, expansion of the stent allows the flexible, constricted configurations to be transformed into a cylinder comprised of substantially rigid rectangular grid geometry. The expanded stent is in the form a hollow tube. Consequently, the stent can be threaded through a body vessel in a flexible, constricted state, and subsequently expanded into a substantially rigid, expanded state for scaffolding against the body vessel wall.

FIGS. 18 and 19 show an embodiment of the stent where joints 38 (between adjacent rings and also forming the rings from straight segments) are circular rather than single connecting dots or points. As shown in the Figures, ring segments 32 (the arrows at the top of the Figure show the direction of stent expansion) and longitudinal connectors 35 are connected at circle joints 38. FIG. 18 shows the stent in a constricted configuration, prior to expansion, while FIG. 19 shows the stent after expansion. Points A–K represent connection points at which the radial ring segments 32 and longitudinal connectors 35 meet the joints 38. Comparing FIGS. 18 and 19, expansion of the stent from a constricted to an expanded configuration causes rotation of the connection points A–K to yield a rectangle-like mesh, in which the corners of the rectangles are occupied by the circular joints. Of course, as discussed, the mesh is in the basic hollow cylinder shape.

Figure 20A:
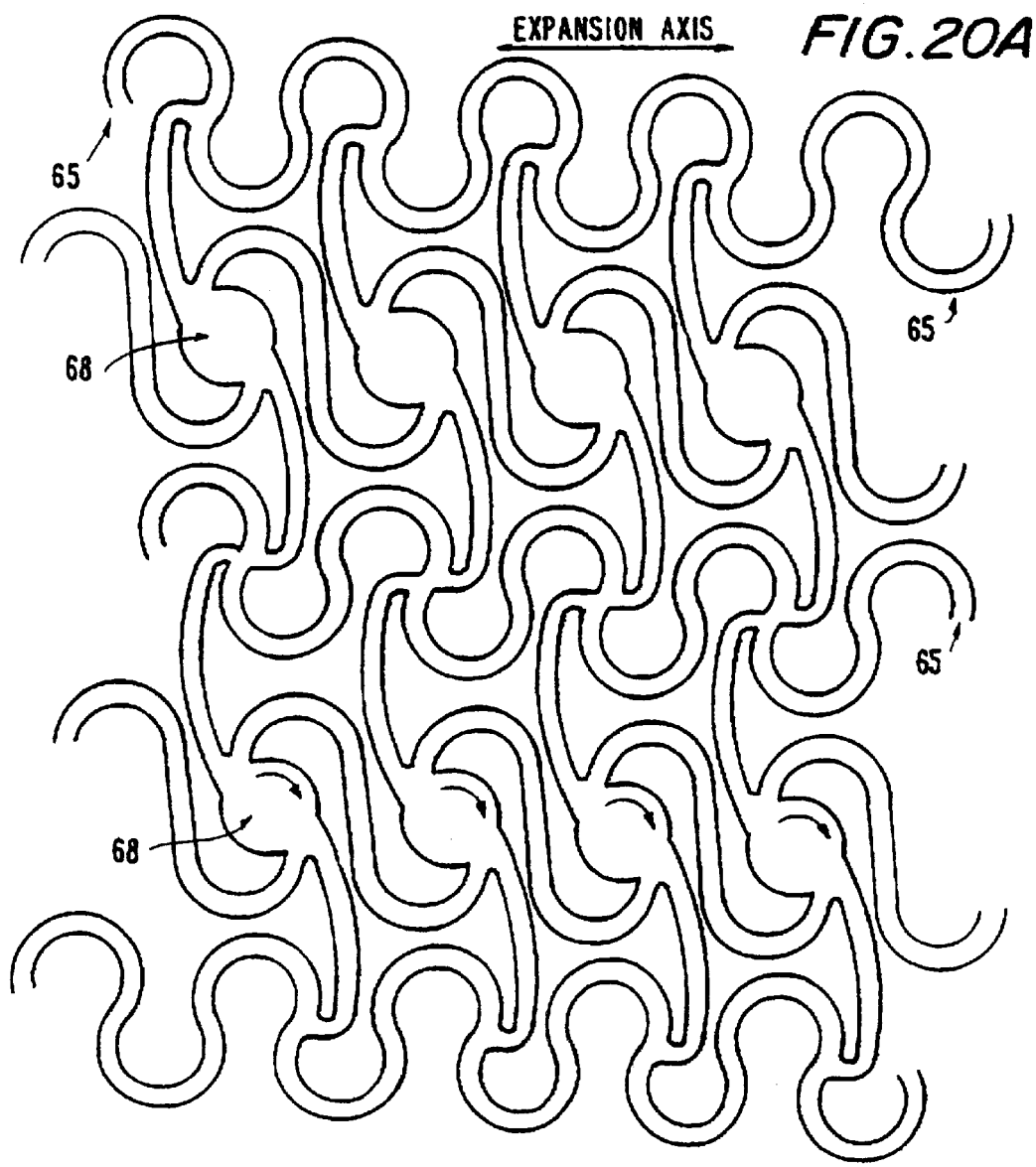
FIG. 20A shows a partial enlarged section of another embodiment of a stent with undulated (opposed, offset U-shapes) rings, strips or segments separating adjacent rings, and alternate rings having simple intersections between adjacent points on the same ring and circular joints between adjacent points.
Figure 20B:
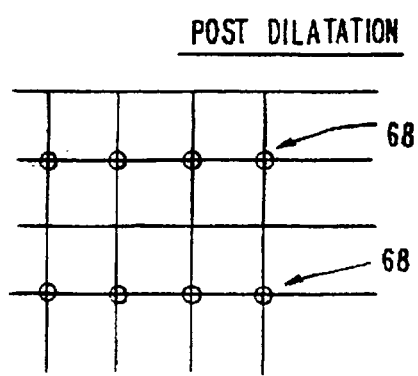
FIG. 20B is a schematic representation of the stent of FIG. 20A in an expanded form.
Figure 22:
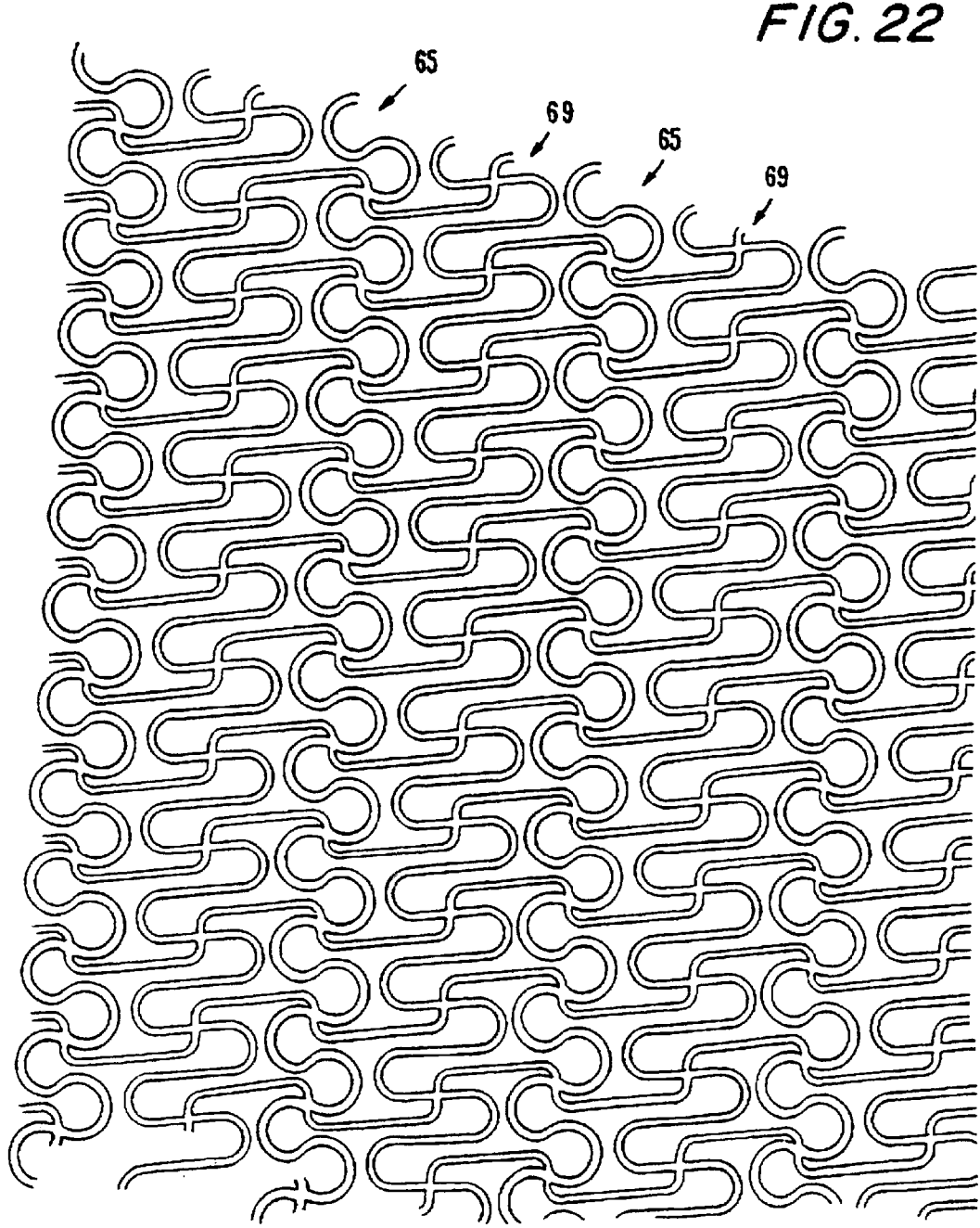

FIGS. 20A and B, 21 and 22 show three embodiments of the stent with undulated or highly curved radially oriented segments 65. In this embodiment, the undulations are opposed, offset U-shapes. Again, the direction of stent, radial expansion is shown on the Figures. FIGS. 20A and 20B, as well as 21 show two differing embodiments of circular or extended joints 68 (FIG. 21 shows hollow circle joints), while FIG. 22 shows a joint 69 which is a point-like intersection of stent ring segments and longitudinal elements. In these embodiments, stent expansion is achieved by rotation of the joints 68 and 69, and by consequent straightening of the undulated or highly curved, radially oriented segments 65. These embodiments allow excellent radial force and tissue scaffolding with minimal shortening along the stent's longitudinal axis. They also allow substantially homogeneous distribution of stress during expansion, with minimal stress and strain on the joints. FIG. 22 shows that every other ring is similar in geometry and thickness to every other ring with adjacent rings having different geometries and material thickness. Of course, the rings of the same geometry and material thickness can either be in phase, with its "peaks" and "valleys" or offset up to about 180 degrees, as shown in FIGS. 27 and 28.

In addition to the improvements provided by the new stent geometry described herein, use of a material such as tantalum can be particularly advantageous. Elongation of tantalum by applying radial expanding balloon pressure can achieve up to a 40% elongation of the stent material. Thus, this elongation of the stent material itself is in addition to the stent radial dilation which can be achieved from expansion of the novel stent by balloon expansion.

As shown in the drawings, the rotation points of the present stents enable large stent expansion, without creating high stress concentration on the connecting points of the stent. This is a significant improvement over both the Palmaz stent and the Pinchansik and Wolff stents of the prior art, in which stress concentration, followed by fatigue and corrosion, at any point, is a potential problem.

Similarly, it is also shown from the descriptions and the Figures that the stent is flexible, longitudinally, when constricted to a small diameter, and becomes stiff, only after expansion. This is also an important improvement over the prior art, as the present stent is not composed of alternating, rigid and articulated components, joined together, but rather is integrally constructed as a single flexible stent, having a long length, and having the ability to bend, homogeneously, along its longitudinal axis when in its constrained form.

Fabrication of the stents shown in FIGS. 1–22 can be accomplished in numerous manners. Two new methods and systems for manufacture of the stents are however, shown in FIGS. 23 and 24.

One current method for fabrication of a patterned etched cylinder is to form a wire mesh from a flat planar surface and then to fuse its two opposite edges to create a cylinder. That method, however, suffers a basic disadvantage in that the presence of the fusing line creates a weakened area along the longitudinal axis of the stent, which is potentially subject to fatigue and breakage. It would be preferable for the stent to be formed from a more uniform piece of material to avoid this potential problem.

According to the present invention, there is, therefore, provided two novel alternative methods for imaging the desired pattern i.e., the location of points, undulating connectors, ring and connecting segments, etc. onto a cylinder, without the need of fusing into a cylinder after forming of the design. Either a film contact imaging method or a laser scanning system can be used to accomplish this objective.

Figure 23:
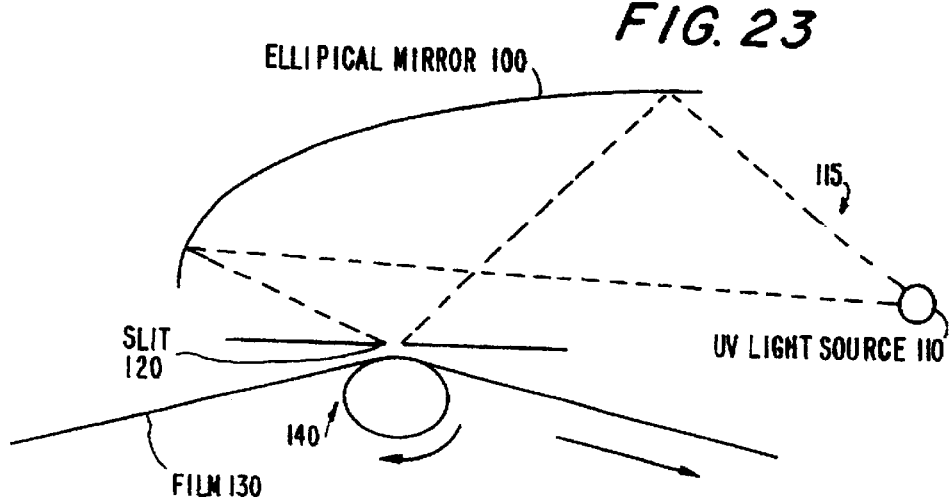
FIG. 23 is a side elevational schematic view of a film contact imaging apparatus for stent manufacture.

As shown in FIG. 23, a film contact imaging method is constructed using an elliptical mirror 100 which reflects ultraviolet light from an ultraviolet light source 110. The ultraviolet light source is located at one focal point of the elliptical mirror 100 and illuminates through a slit or narrow aperture 120 (which eliminates scattered light). Slit or aperture 120 is located at the other focal point of the elliptical mirror to allow for high density power illumination from the ultraviolet source. Rays of ultraviolet light 115 are thus reflected off of elliptical mirror 100 to pass through slit or aperture 120 and onto a moving film 130. Slit 120 extends parallel to the longitudinal axis of hollow tube or cylinder 140. Film 140 carries the design sought to be provided to the tube or cylinder 140.

Film 130 is in contact with hollow cylinder 140. FIG. 22 shows a drawing of the photoetching film for the stent production, according to the method of the present invention. Hollow cylinder 140 is material which is fabricated into the stent of the present invention. Film 130 serves as a mask or template, being transparent to ultraviolet light in some areas and opaque to ultraviolet in others in the predefined stent pattern. Cylinder 140 is coated with an appropriate material (a photoresist) for a photo-etching process. As ultraviolet light 115 is transmitted onto film 130 through slit 120, film 130 moves past cylinder 140 while the cylinder 140 rotates. The rotation of the cylinder 140 is correlated with the movement of the film 130 to appropriately image the pattern on the film around and onto the cylinder 140. As a result, ultraviolet light 115 passing through UV-transparent portions of the film template will strike the cylinder 140 in the desired pattern to photoetch the appropriate configuration onto cylinder 140. An acid treatment is then used to remove the areas which were struck by the UV light. In general, the chemical aspects of the system are similar to that used in the manufacture of computer chips i.e., photoresist, masking, acid, etc.

It should be pointed out that variations on this design can, of course, be accomplished by those of ordinary skill in the art. For example, in the presence of a sufficiently high powered light source, usage of an elliptical mirror is not essential.

Figure 24:
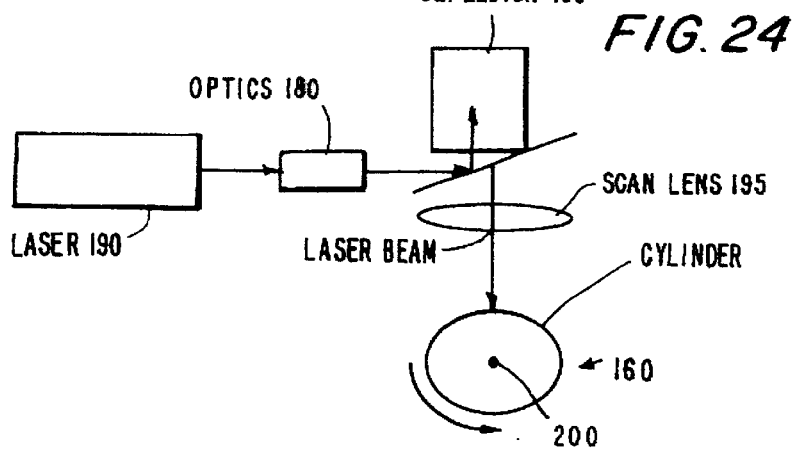
FIG. 24 is a similar schematic view of a laser scanning system for stent manufacture.

As shown in FIG. 24, a second method which can be used for the fabrication of stents is a laser scanning system. The system consists of a cylinder or tube 160 to be etched, a laser 170, the laser optics 180 (containing beam components and modulator), and a dynamic deflector 190 (such as a rotating mirror, a polygon, or any other known scanning deflector). The system is based upon a well-known flat bed scanning system. Cylinder 160 is coated with a photoresist, or material suitable for photoetching. A laser 170 is selected of the appropriate power and wavelength suitable for stimulating the photoresist in use. For example, for an ablation method, the laser can be a high powered IR laser diode; for a photoresist sensitive to visible light, the laser can be a laser in the visible range or for a conventional UV photoresist, an Eximer laser or third (or higher) harmonic generation Nd:YAG/Nd:YLF laser can be used. The laser beam is shaped by an appropriate optical system, and modulated by direct modulation in the case of an IR laser diode, with AOM (an Acoustic Optical Modulator) in the case of a CW laser in the visible, or by a vibrating mirror in the case of a UV laser.

The laser beam from laser 170 hits a deflector device 190 which can be a rotating mirror, a polygon mirror, or other known scanning device. The beam emerges from the deflector, passing through a scan lens 195 and focussed on the cylinder 160. The cylinder, coated with a photoresist, rotates about its longitudinal axis 200 at a constant angular velocity, while the beam scans back and forth. The modulation of the laser beam allows writing a computer imaging file directly on the cylinder without the need of intermediate media (e.g. film). The laser scanning velocity is correlated to the cylinder angular velocity, and is determined by the energy required for exposure of the photoresist.

FIGS. 25 and 26 relate to use of the present invention as a stent graft. This is a stent over which a cloth sleeve is positioned to prevent blood from going through the stent wall or for having better support of the vessel wall. As a particular embodiment, the stent graft is in a Y-shape for the treatment of aortic aneurysm, near the aortic bifurcation. In such cases, simple tube stent grafts tend to migrate downwardly. In the Y-shape of the present invention, however, the stent is supported on the bifulcation and thus it cannot migrate from the site. A method of percutaneous insertion of this Y-stent graft is shown in the drawing. As shown in the drawings, the main tube integral with a right and a left tube, thereby forming the Y-shape stent graft. A first balloon passes from the left tube into the main tube while a second balloon passes into the right tube. During deployment, the right tube moves flexibly to the right. The second step of deployment contemplates the pulling of the entirety of the stent graft so that it is located and fixed to the aortic bifulcation. Then inflation of balloon No. 1 for the main tube is accomplished. Then balloon No. 2 is inflaated in the right tube. Then balloon No. 1 is pulled and reinflated followed by a withdrawal of balloons. FIG. 25 shows the Y-shaped tube stent graft in its open or expanded configuration. Balloon No. 1 is shown inflated and located in the main graft tube. Balloon No. 2 is shown in the right graft tube. Pulling balloon No. 1 and reinflating the same expands the left graft tube.

Having described this invention with regard to specific embodiments, it is to be understood that the description is not meant as a limitation since further variations or modifications may be apparent or may suggest themselves to those skilled in the art. It is intended that the present application cover such variations and modifications as fall within the scope of the appended claims.

I claim:

1. A medical stent, comprising:
at least two radial rings, each of said radial rings having windings, each of said rings having both a constricted state and an expanded state corresponding to the constricted state and expanded state of said windings of said stent, said constricted state being state of said rings in which said windings are curled in shape, said expanded state being a state of said rings in which said windings are uncurled in shape such that each of said rings becomes substantially circular and of greater diameter than said ring in said constricted state; and, longitudinal connectors, said longitudinal connectors connecting said radial rings to form said stent in a cylindrical shape, said of said stent allowing delivery of said stent on a catheter into a patient, and said expanded state of said stent causing said rings to rest against the walls of a body vessel into which said stent is placed, said rings being selectively expandable from said constricted state to said expanded state, said stent being flexible along substantially its entire longitudinal axis when said stent is in said constricted state, said stent being substantially rigid when said stent is expanded to said expanded state, and said stent being substantially the same length independent said of whether said rings or said stent are in said constricted or said expanded states wherein at least part of a first winding has at least a portion thereof selectively removed.

2. A medical stent as claimed in claim 1 wherein said stent is expandable by a balloon catheter.

3. A medical stent as claimed in claim 1, wherein said rings have points on said windings, said points rotating forty-five (45) degrees upon expansion of said rings from said constricted state to said expanded state.

4. A medical stent as claimed in claim 1, wherein said rings have points on said windings, said points rotating ninety (90) degrees upon expansion of said rings from said constricted state to said expanded state.

5. A medical stent as claimed in claim 1, wherein said rings have points on said windings, said points rotating one hundred and eighty (180) degrees upon expansion of said rings from said constricted state to said expanded state.

6. A medical stent as claimed in claim 1, wherein said rings have points on said windings, said points rotating three hundred and sixty (360) degrees upon expansion of said rings from said constricted state to said expanded state.

7. A medical stent as claimed in claim 1, wherein said rings have at least two points on said windings, at least one of said points rotating forty-five (45) degrees in a first direction and at least one of said points on said same ring rotating ninety (90) degrees in a direction opposite to said first direction.

8. A medical stent as claimed in claim 1, wherein at least two of adjacent rings are paired, the winding of a said second ring of said pair being the mirror image of the winding of said first ring of said pair.

9. A medical stent as claimed in claim 1, wherein said longitudinal connectors are substantially straight when said stent is in said constricted state.

10. A medical stent as claimed in claim 1, wherein said longitudinal connectors are substantially straight both when said stent is in said constricted state and when said stent is in said expanded state.

11. A medical stent as claimed in claim 1, wherein said longitudinal connectors are curved when said stent is in said constricted state, and become straight when said stent expands into said expanded state.

12. A medical stent as claimed in claim 1, wherein at least one of said longitudinal connectors between adjacent of said rings is omitted.

13. A medical stent as claimed in claim 1, wherein at least one segment of at least one of said rings is omitted.

14. A medical stent as claimed in claim 1, wherein the shape of said stent in said expanded state is a hollow cylinder of substantially rigid rectangular mesh.

15. A medical stent as claimed in claim 1, further comprising rotatable joints on at least one of said rings.

16. A medical stent as claimed in claim 15, wherein said rotatable joints are circular.

17. A medical stent as claimed in claim 15, wherein said rotatable joints are points of connection between said rings and said longitudinal connectors.

18. A medical stent as claimed in claim 15, wherein said rotatable joints are circular and hollow.

19. A medical stent as claimed in claim 1, wherein at least some of either said rings or said longitudinal connectors comprise undulating segments.

20. A medical stent as claimed in claim 19 wherein said undulating segments are opposed and offset U-shapes.

21. A medical stent as claimed in claim 15 wherein at least two of adjacent rings are paired, said rings comprise peaks and valleys and and said peaks and valleys are offset with respect to one another by about 0 to 180 degrees.

22. A medical stent as claimed in claim 1, in which at least part of said stent is comprised of tantalum.

23. A medical stent as claimed in claim 3, wherein said windings also will rotate one hundred and eighty (180) degrees opposite to said rotation of forty-five (45) degrees upon expansion of said stent from said constricted state to said expanded state.

* * * * *